US006981967B2

(12) United States Patent
Massengale et al.

(10) Patent No.: US 6,981,967 B2
(45) Date of Patent: Jan. 3, 2006

(54) LARGE VOLUME BOLUS DEVICE AND METHOD

(75) Inventors: Roger Dillard Massengale, Mission Viejo, CA (US); Kenneth W. Rake, Laguna Niguel, CA (US); Eric Mabry, Trabuco Canyon, CA (US)

(73) Assignee: I-Flow Corporation, Lake Forest, CA (US)

( * ) Notice: Subject to any disclaimer, the term of this patent is extended or adjusted under 35 U.S.C. 154(b) by 0 days.

(21) Appl. No.: 10/162,089

(22) Filed: Jun. 3, 2002

(65) Prior Publication Data

US 2003/0040722 A1 Feb. 27, 2003

Related U.S. Application Data

(60) Provisional application No. 60/295,070, filed on Jun. 1, 2001.

(51) Int. Cl.
*A61M 5/32* (2006.01)
*A61M 5/16* (2006.01)
*A61M 5/14* (2006.01)

(52) U.S. Cl. .................. 604/174; 604/518; 604/80; 604/255

(58) Field of Classification Search .......... 604/80–518; 606/236; 215/11.1–11.6, 12.2
See application file for complete search history.

(56) References Cited

U.S. PATENT DOCUMENTS

| 4,432,754 A * | 2/1984 | Urquhart et al. ............. 604/518 |
| 4,573,974 A * | 3/1986 | Ruschke ....................... 604/81 |
| 5,011,477 A | 4/1991 | Winchell et al. |
| 5,080,652 A | 1/1992 | Sancoff et al. |
| 5,152,753 A | 10/1992 | Laguette et al. |
| 5,224,934 A | 7/1993 | Payne et al. |
| RE35,187 E | 3/1996 | Gortz |
| 5,505,707 A | 4/1996 | Manzie et al. |
| 5,776,105 A * | 7/1998 | Corn .......................... 604/174 |
| 5,807,312 A | 9/1998 | Dzwonkiewicz |

(Continued)

FOREIGN PATENT DOCUMENTS

WO    WO 00/71190    11/2000

*Primary Examiner*—Nicholas D. Lucchesi
*Assistant Examiner*—Roz Maiorino
(74) *Attorney, Agent, or Firm*—Knobbe Martens Olson & Bear LLP

(57) ABSTRACT

A device and method for the infusion of medicinal fluid at a controlled flow rate to a wound site or the blood stream of a patient is disclosed. A pump delivers fluid under pressure from a fluid source through a continuous and substantially constant flow path and through a supplemental bolus dose flow path. A large volume bolus dose reservoir accumulates a large quantity of fluid from the bolus dose flow path and holds the fluid under pressure. A flow regulator controls the fill rate of the large volume bolus reservoir. The large volume supplemental bolus dose is released from the bolus reservoir upon patient activation of a valve. The release rate of the bolus dose is controlled by the decompression of an elastomeric sphere or spring chamber, by the pressure gradient at the valve and/or by optional flow control tubing. In one embodiment, a source of fluid under pressure is pumped at a continuous and substantially constant rate to a wound site or the blood stream of a patient and into a bolus syringe, which is capable of holding a large quantity of fluid under pressure. A plunger on the bolus syringe may be depressed to release a bolus dose of fluid into a chamber accumulator and then to the patient at a controlled release rate.

18 Claims, 3 Drawing Sheets

U.S. PATENT DOCUMENTS

| | | |
|---|---|---|
| 5,810,783 A | 9/1998 | Claro |
| 5,891,102 A | 4/1999 | Hiejima et al. |
| 5,906,597 A | 5/1999 | McPhee |
| 6,045,533 A | 4/2000 | Kriesel et al. |
| 6,206,850 B1 * | 3/2001 | O'Neil ........................ 604/80 |
| 6,213,972 B1 | 4/2001 | Butterfield et al. |
| 6,213,981 B1 | 4/2001 | Hiejima et al. |

* cited by examiner

LARGE VOLUME BOLUS DEVICE AND METHOD

PRIORITY INFORMATION

This application is related to, and claims priority from, U.S. Provisional Patent Application No. 60/295,070, filed Jun. 1, 2001, the entirety of which is incorporated by reference herein.

BACKGROUND OF THE INVENTION

1. Field of the Invention

This invention relates to a device and method for administering a quantity of fluid to a wound site nerve bundle, or the blood stream of a patient. More specifically, this invention relates to an improved device and method for the activation of a supplemental large volume, flow-controlled bolus dose of fluid by itself or during a continuous primary infusion of fluid.

2. Description of Related Art

In instances of severe pain, infection, and other medical ailments, it has been proven beneficial to administer a continuous flow of medicinal fluid to a patient. There are many types of medicinal fluids that can be administered in this manner including, but not limited to, insulin, analgesics and antibiotics. In some instances, it is beneficial to administer a supplemental bolus dose of the medicinal fluid to a patient who is also receiving a continuous primary flow of the fluid.

The continuous delivery of such medicinal fluids over extended periods of time has required prolonged hospital stays and monitoring by medical staff. The possibility of reducing hospital stays has prompted research and development in the area of self-administration of such fluids by patients. As a result, there are several patient controlled administrative devices, ("PCA devices") on the market. Certain PCAs enable patients to self-administer continuous as well as bolus doses of medicinal fluids. Some of these PCAs are fairly mobile and provide for a continuous or basal rate of fluid, which is the on-going continuous primary flow rate of fluid to a patient. Some PCAs also permit a supplemental or bolus dose of fluid to be administered.

However, there are dangers associated with the self-administration of certain medicinal fluids. Patients may not properly control the amount of fluid they receive and the time period during which they receive it. In particular, over-administration of analgesics, for example, may result in nausea, bowel, urinary and motor dysfunction, and even death. Many of the PCAs already on the market only provide for an on-demand rush of the medicinal fluids, whereby patients are expected to remember to turn off the bolus flow of fluid. The possibility of human error increases the risk of patient over-administration. Therefore, recent activity has been directed toward developing mobile PCAs which control both the rate of the continuous fluid and the amount of the bolus dose fluid which a patient may self-administer.

One such prior art PCA device as disclosed in U.S. Pat. No. 5,011,477 (the "Baxter device"). One major problem with this invention is that the bolus reservoir is severely inadequate for the administration of large volume bolus doses of medicinal fluid. Certain medicinal fluids, such as antibiotics, or low concentration analgesics require large volume bolus doses, such as 2–10 cc's or more of fluid per dose. Such large bolus requirements exceed the bolus dose capacity provided for in the Baxter device. It has been shown that 10 cc bolus sizes are very efficacious in wound site and nerve block procedures. New pain protocols emphasize lower concentrations and higher flow rate and larger bolus sizes. While overall dosages of medication are similar to high concentration, low flow rate protocols, the new method is preferred as safer. As a result, the bolus size requirements have been increasing. Baxter's 0.5 cc bolus device is not adequate when used with low concentrations.

The Baxter device and some other prior art PCAs require manual squeezing or pushing to release the bolus dose. A major problem with such manual squeezing or pushing is that the manual force required to administer the bolus dose is a direct function of the size of the bolus reservoir volume. The higher the bolus volume, the more squeezing or pushing force is required to release the bolus dose. Weak patients may not have the strength to self-administer large volume bolus doses in this manner.

Prior art PCAs do not control the release rate of the bolus dose to the patient or are not equipped to efficiently control the release rate of a large volume bolus of fluid. It is important to control the release rate of a bolus dose of fluid because there is a risk of injury or complication from the quick release of bolus doses and bolus doses of certain medicinal fluids should not be released into the patient all at once, but over a specified period of time. This risk increases with the size of the bolus dose required.

One prior art device, such as that disclosed in U.S. Pat. No. 6,045,533 attempts to control the release rate of the bolus dose to the patient through the use of a rotating drive wheel. However, one significant drawback of this device is that a patient cannot be expected to manually rotate a drive wheel continuously for a period of 5 minutes, which is approximately the amount of time during which a large volume bolus dose of about 10 cc's should be administered.

What is thus needed is a mobile device and method to provide a continuous and substantially constant flow of medicinal fluid and which provides a controlled, large volume supplemental bolus dose of medicinal fluid whereby the patient need not be relied upon to manually control the release rate of the large volume bolus dose. Further, an improved activation device and method is needed such that even a weak patient may administer a large bolus dose.

SUMMARY OF THE INVENTION

The present invention is directed to a patient-controlled administration device and method for the continuous delivery of fluid and is particularly designed for the self-administration of large volume supplemental bolus doses of medicinal fluid. This device and method does not require a patient to turn off the bolus dose, or to muster enough strength to manually force the release of a large bolus dose.

One embodiment of the present invention provides a device comprising a source of fluid under pressure for forcing fluid through a continuous or primary flow path as well as through a bolus flow path for delivery into the wound site or the blood stream of a patient. A large volume bolus reservoir accumulates a large quantity of fluid from the bolus flow path and holds the fluid under pressure until the bolus dose is triggered for release into the patient.

The continuous flow path contains a flow regulator, which controls the primary flow rate of fluid to the patient. The flow regulator may also be adjusted to regulate the continuous flow rate.

The bolus reservoir accumulates a large quantity of fluid as compared to other PCA devices currently on the market. It is advantageous for the bolus reservoir to hold somewhere between 2–10 cc's of fluid, which is the proper safe dose of local anesthetics administered in a bolus dose. The fill-rate of the bolus reservoir is controlled by a flow regulator in the bolus dose flow path, and the fill-volume of the bolus reservoir is controlled by a non-resilient housing.

In operation, a valve in the bolus flow path is manually triggered, allowing fluid under pressure in the bolus reservoir to flow toward the patient. The release rate of the bolus dose through the bolus dose flow path to the patient is controlled by the configuration of the bolus reservoir which may be an elastomeric sphere or spring chamber, by the valve, or by optional flow control tubing.

In another embodiment of this device, a pump forces fluid, contained under pressure, through a continuous flow path toward the wound site or the blood stream of a patient and also through a valve to accumulate inside a syringe chamber capable of holding a large quantity of fluid under pressure. A check valve prevents flow downstream from the syringe chamber until the chamber reaches a specific fill-pressure.

When depressing the syringe plunger, a bolus dose of fluid is quickly released from the bolus syringe chamber into the continuous flow path. This channels the bolus dose downstream through the check valve and into a large volume bolus chamber accumulator. Fluid flows from the chamber accumulator through the flow path and into the patient at a rate preferably controlled by the downstream tubing. This embodiment prevents a patient from receiving too much bolus fluid at one time and functions to ease patient effort in administering a large volume bolus dose.

Further aspects, features and advantages of the present invention will become apparent from the following drawings and detailed description intended to illustrate but not to limit the concepts of the invention.

DETAILED DESCRIPTION OF THE PREFERRED EMBODIMENTS

Figure 1:
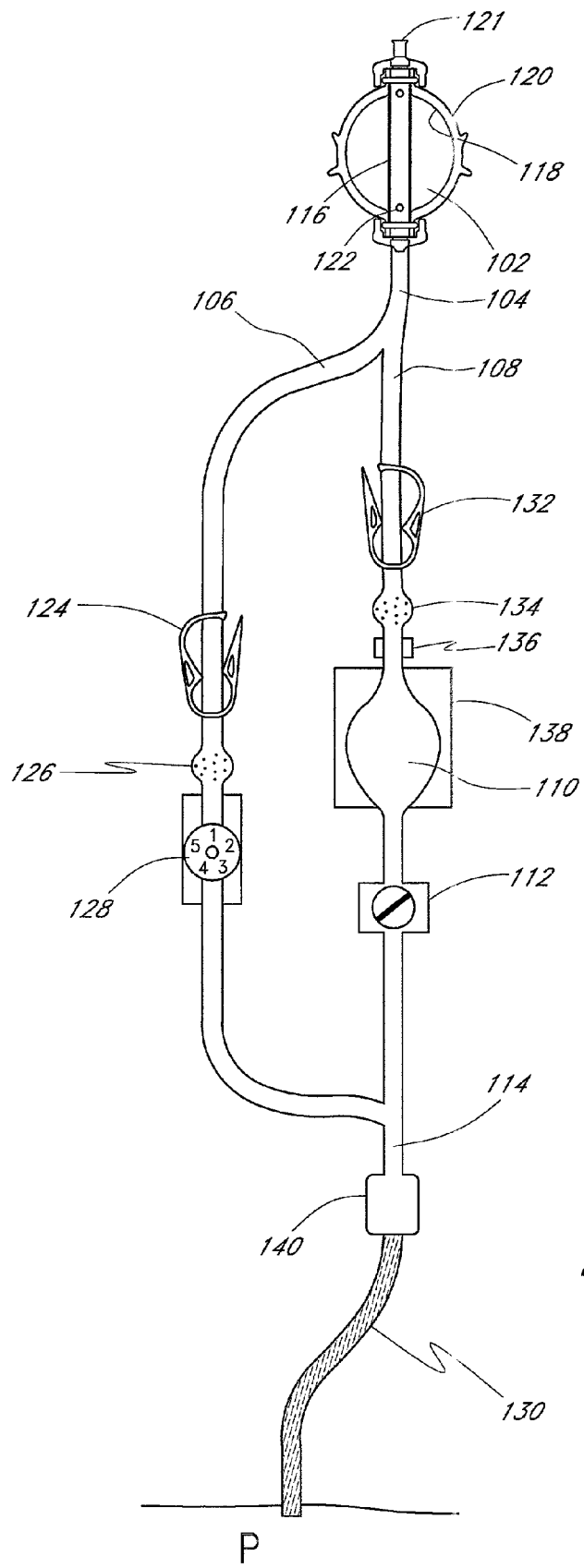
FIG. 1 is a schematic view of one embodiment of the fluid dispensing device and method of the present invention.

Referring now to the drawings, FIG. 1 illustrates a schematic view of one embodiment of the fluid dispensing device and method. The device comprises a pressurized fluid source or pump 102 that holds medicinal fluid, such as local anesthetics. The pump 102 forces the medicinal fluid through a conduit 104. The conduit 104 splits into a continuous or primary flow path 106 and into a controlled bolus flow path 108 for delivery into a wound site nerve bundle or the blood stream of a patient P. A large volume bolus reservoir 110 accumulates a large quantity of fluid from the bolus flow path 108 and holds the fluid under pressure until the bolus dose is triggered by an actuator 112 for release into the patient P. Downstream from the bolus reservoir 110, the continuous flow path 106 and the bolus dose flow path 108 converge into a single flow path 114 to the patient P.

The pump 102 preferably accommodates about from 100 to 500 ml of fluid under 10–15 psi. The pump 102 has an inner core 116 surrounded by an elastomeric chamber 118 within a housing 120. The core 116 preferably has an inlet port 121 to fill the pump and an outlet port 122 in fluid communication with the tubing 104. The elastomeric chamber 118 is preferably constructed from a resilient material which may comprise a variety of elastomeric compositions, well known in the art, including vulcanized synthetic polyisoprenes, natural latex, natural rubber, synthetic rubber or silicone rubber. Fluid is held under pressure within the elastomeric chamber 118 and flows from the elastomeric chamber 118 through an outlet port 122 into the conduit 104 at a controlled and predictable rate. Alternatively, conduit 104 may be sized to serve as a flow restrictor. The illustrated pump 102 is described in U.S. Pat. No. 5,254,481 assigned to I-Flow Corporation, which is hereby incorporated by reference. A variety of other conventional pumps may be used, so long as they can impart the desired pressure on the fluid. For example, the pumps described in U.S. Pat. Nos. 5,080,652 and 5,105,983 both assigned to I-Flow Corporation, which are hereby incorporated by reference may also be used, as well as other suitable electronic or mechanical pumps offered by other manufacturers as will be understood by those of skill in the art.

An optional clamp 124 is positioned in the flow pat 106 downstream from the conduit 104. The clamp 124 can compress the flow path 106 such that fluid flow from the pump 102 is occluded. Such occlusion is advantageous for the transportation and preparation of the fluid delivery device and method as described herein. The illustrated clamp 124 is also described in U.S. Pat. No. 6,350,253 assigned to I-Flow Corporation, which is hereby incorporated by reference. However, a variety of other conventional clamps known in the industry may be used to occlude the flow of fluid from the pump 102 through the flow path 106 such as compression clamps, C clamps, roller clamps, and the like.

An optional filter 126 downstream of the clamp 124 separates the fluid from contaminates and other undesired particles that may be found within the fluid. The filter 126 also preferably eliminates air from the fluid path 106. One such filter 126 is described in U.S. Pat. No. 6,350,253 assigned to I-Flow Corporation, which is hereby incorporated by reference. Other suitable filters recognized in the industry may be used to capture undesired particles and/or remove air from the system.

A flow regulator 128 is positioned in the continuous flow path 106. The flow regulator 128 sets the continuous and substantially constant flow rate of fluid, preferably at 2–5 cc's per hour, from the pump 102 to the patient P via tubing 106. One such flow regulator 128 is described in U.S. Pat. No. 6,350,253 assigned to I-Flow Corporation, which is hereby incorporated by reference. Other suitable flow regulation devices may be used to control the flow of fluid including, but not limited to, a catheter 130. The flow regulator 128 may be manually adjustable, if desired, and provided with a dial, switch or lever with an adjustable flow rate control display of 1–5 cc's of fluid per hour. Alternatively, a constant flow regulator which may not be adjusted can be employed. The particular arrangement of the clamp 124, filter 126 and flow regulator 128 herein described is merely exemplary. These elements, if present, may be arranged in any order as will be easily understood by those skilled in the art.

Still referring to FIG. 1, an optional clamp 132 is positioned in the flow path 108 downstream from the conduit 104. The clamp 132 can compress the flow path 108 such that fluid flow from the pump 102 is occluded. Such occlusion is advantageous for the transportation and preparation of the fluid delivery device and method as described herein. The illustrated clamp 132 is also described in U.S. Pat. No.

6,350,253 assigned to I-Flow Corporation, which is hereby incorporated by reference. However, a variety of other conventional clamps known in the industry may be used to occlude the flow of fluid from the pump 102 through the flow path 108 as discussed above.

An optional filter 134 downstream of the clamp 132 separates the fluid from contaminates and other undesired particles that may be found within the fluid. The filter 134 also preferably eliminates air from the fluid path 108. One such filter 134 is described in U.S. Pat. No. 5,350,253, assigned to I-Flow Corporation, which is hereby incorporated by reference. Other suitable filters recognized in the industry may be used as well.

A flow regulator 136 may be positioned downstream of the filter 134, although the particular arrangement of the clamp 132, filter 134 and flow regulator 136, if present, herein described is merely exemplary. The flow regulator 136 sets the bolus dose fill-rate into the bolus reservoir 110 at an approximate rate of 5–10 cc's an hour. One designed flow regulator 136 is described in U.S. Pat. No. 6,350,253 assigned to I-Flow Corporation, which is hereby incorporated by reference. Other flow regulators may also be used.

The large volume bolus reservoir 110 is constructed from a resilient material which may comprise a variety of elastomeric compositions, well known in the art, including vulcanized synthetic polyisoprenes, natural latex, natural rubber, synthetic rubber or silicone rubber, giving the bolus reservoir 110 high elasticity. As fluid flowing through the regulator 130 enters the bolus reservoir 110 at a controlled rate, the reservoir 110 expands until it reaches a maximum capacity such as 5 or 10 cc's of fluid, or any other amount that is safe to be administered to the patient P in accordance with the present invention. A nonresilient container 138 preferably prevents the bolus reservoir 110 from expanding beyond its maximum capacity. Alternatively, the elasticity of the reservoir may control the maximum capacity of the container 138.

The patient operable bolus actuator 112 in a simple form is a valve positioned in the bolus dose flow path 108 downstream from the bolus reservoir 110. The bolus valve 112 may take the form of a push-button, stopcock, or other suitable valve. When the valve 112 is opened, the bolus dose of fluid is released from the bolus reservoir 110 into the bolus flow path 108. Fluid from the bolus dose flow path 108 and fluid from the continuous flow path 106 flows into the flow path 114 and into the patient P. A luer lock 140 may be positioned in the flow path 114. The catheter 130 connects to the luer lock 140. The actuator may take forms other than a valve. For example, it may be another form of release device so long as it has the important characteristics of (1) not requiring effort to force fluid out of the chamber, and (2) once activated, the fluid is released without requiring further action by the patient.

The release-rate of the bolus dose to the patient P is controlled by the decompression of the elastomeric bolus reservoir 110, by the pressure gradient at the valve 112, and the diameter of the catheter 130 or some other form of flow control tubing. Advantageously, the patient P does not have to provide pressure to force fluid out of the large volume bolus reservoir 110 into the narrower bolus flow path 108. Rather, the patient P can turn the stopcock or release the push button to administer the bolus dose. If the patient P activates the bolus valve 112 prior to the time the bolus reservoir 110 has filled to its capacity, the patient P receives less than the full amount of the bolus dose. In effect, this prevents the patient P from self-administering more than the maximum desired amount of fluid per the time specified as a large volume bolus dose.

If desired, the valve 112 can be of the type which must be held open, or it could provide a timed release. The valve could be pressure responsive such that when opened, it will remain open until the pressure drops to a certain level, such as 1 psi.

Figure 2:
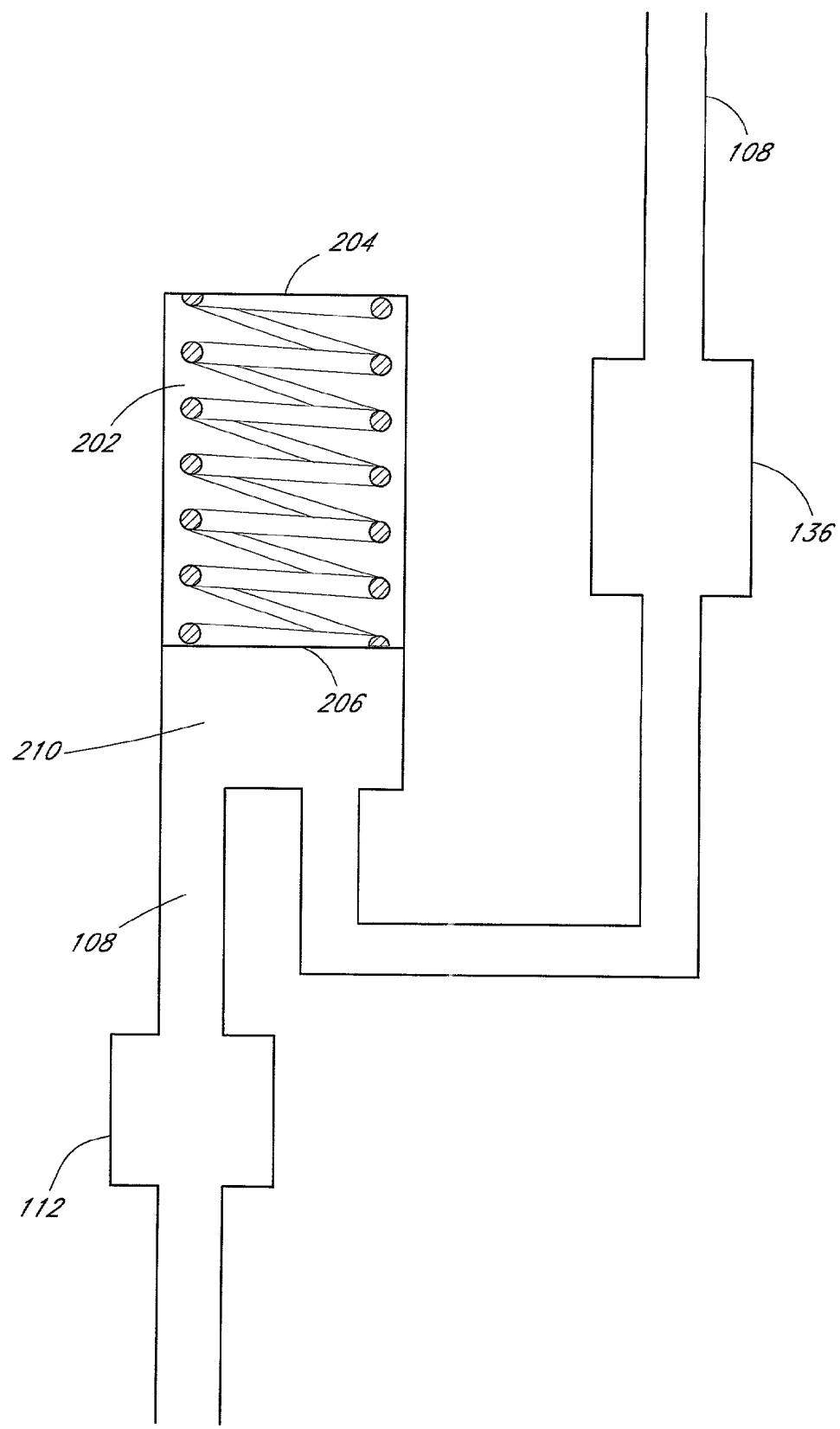
FIG. 2 is a view of another embodiment of a bolus reservoir used in the controlled bolus flow path of the fluid dispensing device and method of the present invention.

FIG. 2 is a view of another embodiment of a bolus reservoir 210 configured as a spring chamber. In this embodiment, a compression spring 202 is contained within the chamber 210. The spring 202 extends between a back plate 204 and a retractable wall 206 or platen of the chamber 210. When the chamber 210 contains no fluid, the spring 202 is not compressed. As fluid from the flow regulator 136 enters the chamber 210, the incoming fluid exerts pressure onto the back plate 206, compressing the spring 202. When the spring 202 is compressed, the bolus syringe chamber 210 may hold about 10 cc's of fluid at about 2–6 psi of pressure. When the patient P activates the valve 112, the bolus dose of fluid empties from the chamber 210 into the controlled bolus flow path 108 and toward the patient P.

Figure 3:
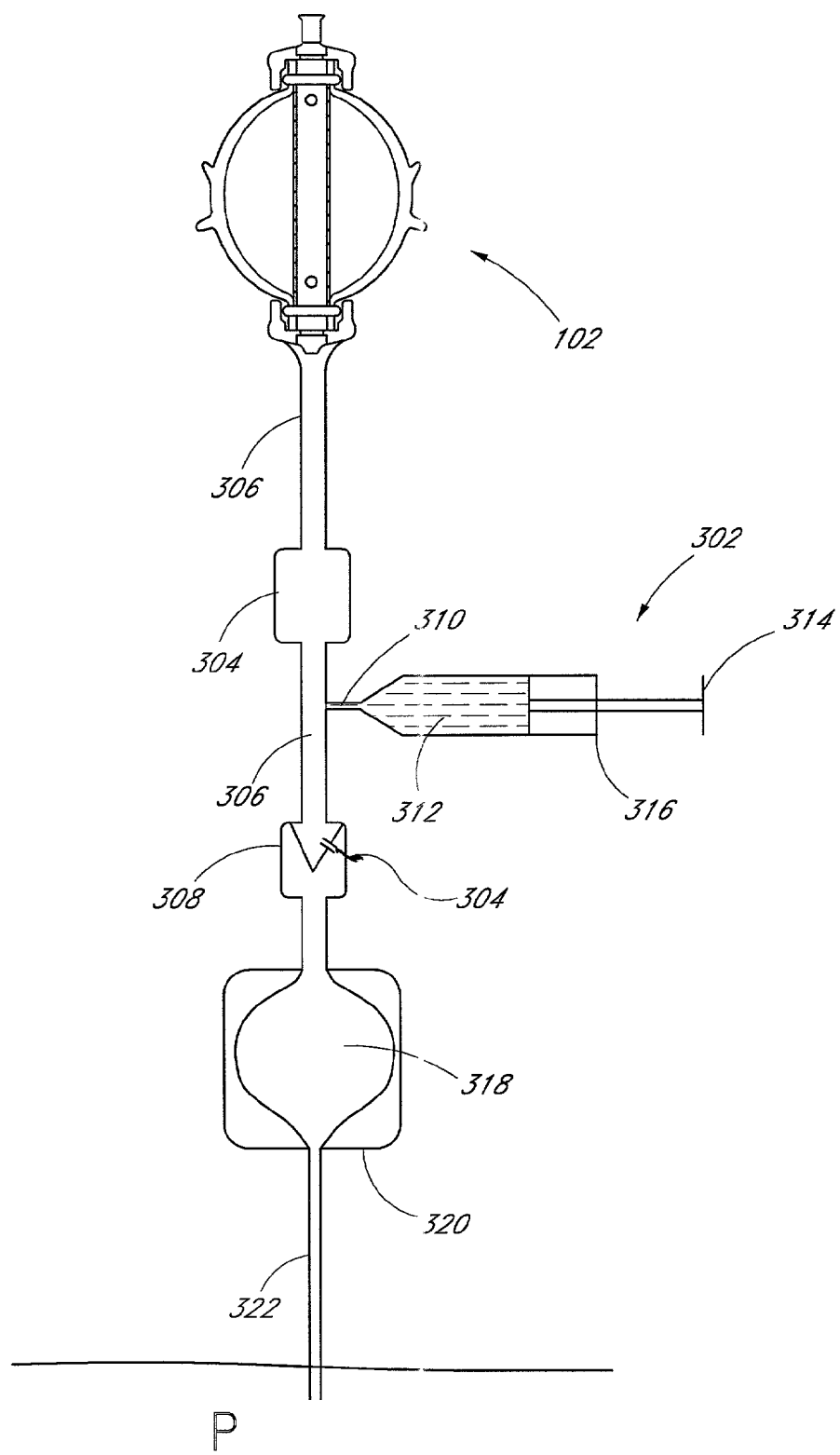
FIG. 3 is a schematic view of another embodiment of the fluid dispensing device and method of the present invention.

FIG. 3 illustrates a schematic view of another embodiment of the fluid dispensing device and method of the present invention utilizing a bolus syringe 302. The bolus syringe 302 may embody any typical syringe commonly used in the medical field. A lockout orifice 304 is positioned in flow path 306 downstream from the pump 102 and upstream from the syringe 302. The lockout orifice 304 serves as a one-way flow restrictor and a check valve which sets the flow of fluid at a preferable rate of 5–10 cc's per hour.

Where a separate continuous flow path 106 is used, as illustrated in FIG. 1, then a check valve 308, which is positioned in the flow path 306 downstream from the syringe 302 requires a pressure greater than the bolus filling pressure to open. In such an embodiment, the pump 102 forces fluid downstream into the separate continuous flow path 106 as well as into the bolus flow path 306. As fluid flows into the bolus flow path 306, it flows through the lockout orifice 304 and into a bolus syringe chamber 312, which is capable of holding about 5–10 cc's of fluid under pressure.

Where there is no continuous flow path 106 separate from flow path 306, the check valve 308 may be configured to allow for a continuous flow of fluid as well as a bolus dose of fluid, and the bolus dose of fluid is prevented from flowing to the patient P unless the fill pressure at the bolus syringe chamber 312 reaches a certain level. As fluid from the pump 102 flows through the lockout orifice 304, a fraction of the fluid flows through a small opening 369 in the check valve 308 for continuous administration of fluid to the patient P at a rate of 1–5 cc's per hour. The rest of the fluid is prevented from flowing through the check valve 308 and flows into an inlet port 310 of a bolus syringe chamber 312. The check valve 308 requires a pressure greater than the bolus filling pressure to open.

A plunger 314 of the syringe 302 has a typical T-shape for grasping or squeezing. When the bolus reservoir chamber 312 contains no fluid, the plunger 314 is flush with a distal end of the syringe 316. When the bolus syringe chamber 312 is filled to a capacity of about 1–30 cc's of fluid, the plunger 314 is extended away from the distal end of the syringe 316. When the bolus dose is to be administered, the plunger 314 can be manually depressed toward the syringe 316, causing the pressurization of fluid within the chamber 312. This causes the fluid within the syringe chamber 312 to empty from the syringe chamber 312 through the outlet port 310 and into the flow path 306. The lockout orifice 304 prevents the bolus dose from flowing upstream toward the pump 102, thereby channeling the bolus dose downstream toward the check valve 308. The pressure of the bolus dose forces open the second conduit or opening in the valve 308 and the bolus fluid flows through the valve 308 and into a chamber accumulator 318. This allows the syringe chamber 312 to empty so that there is no need for the patient P to continue depressing the syringe plunger 314. It also eases the force that must be applied to depress the plunger 314.

The chamber accumulator 318 may take the form of an elastomeric sphere housed in a nonresilient container 320, but the chamber accumulator 318 need not take this particular form. A catheter 322 or some other form of a flow control conduit may be positioned downstream of the chamber accumulator 318, and the catheter 322 has a diameter that dispenses fluid to the patient P at a predictable rate, preferably a maximum of 10 cc's of fluid over 5 minutes, regardless of how fast the plunger 314 is depressed. This embodiment of the present invention works well for the safe administration of local anesthetics and multi-dose antibiotics over a predictable period of time, and functions to override human error or misprecision in the administration of such large volume bolus doses.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above, but should be determined only by a fair reading of the claims that follow.

What is claimed is:

1. A device for dispensing fluid to a patient comprising:
   a first reservoir configured to provide a source of fluid under pressure;
   a bolus flow path for the delivery of a bolus dose of fluid;
   a large volume bolus reservoir in fluid communication with said bolus flow path and configured to receive fluid from said first reservoir, said bolus reservoir being configured to elastically expand to pressurize fluid, store the pressurized fluid and dispense the pressurized fluid; and
   a patient operable actuator to release fluid from the bolus reservoir, said actuator being configured such that it does not require effort to force the fluid out of the bolus reservoir and that when actuated by the patient, fluid is permitted to flow out of the bolus reservoir to the patient without further action by the patient.

2. The device of claim 1, including a continuous flow path from the source providing a continuous and substantially constant flow rate of fluid, and wherein the continuous flow path and bolus flow path are in fluid communication with the source of fluid.

3. The device of claim 2, including a flow regulator which sets the flow rate through the continuous flow path into the patient.

4. The device of claim 2, wherein said paths converge into a single path downstream from said valve.

5. The actuator of claim 2, wherein the continuous flow path further comprises an adjustable flow regulator.

6. The device of claim 2, wherein the continuous flow path further comprises an adjustable flow regulator for the manual adjustment to 1–5 cc's of fluid per hour.

7. The device of claim 1, including a flow regulator which sets the flow rate of fluid through the bolus flow path.

8. The device of claim 1, wherein said bolus reservoir comprises an elastomeric chamber for holding a bolus volume of fluid under pressure to be delivered on demand at a controlled rate to a patient.

9. A device for dispensing fluid to a patient, comprising:
   a fluid pump configured to supply a source of fluid under pressure;
   a continuous flow path in communication with the fluid pump, the continuous flow path configured to deliver a continuous dose of fluid;
   a manually-adjustable flow regulator configured to regulate a flow rate within the continuous flow path;
   a bolus flow path in communication with the fluid pump, the bolus flow path configured to deliver a bolus dose of fluid;
   a bolus reservoir in communication with the bolus flow path, the bolus reservoir configured to receive and store fluid from said fluid pump and selectively permit fluid to be dispensed; and
   a patient operable actuator configured to dispense fluid from the bolus reservoir.

10. The device of claim 9, wherein the flow regulator is a valve including a dial to permit adjustment of a flow rate through the flow regulator.

11. The device of claim 10, wherein the flow regulator includes a display configured to indicate a flow rate of fluid through the flow regulator.

12. The device of claim 9, wherein the flow regulator permits adjustment of a flow rate through the flow regulator of between about 1 and 5 cc's of fluid per hour.

13. The device of claim 9, wherein the bolus reservoir comprises an expandable, elastomeric reservoir member.

14. The device of claim 9, wherein the bolus reservoir comprises a spring-biased piston.

15. The device of claim 9, wherein the actuator comprises a valve.

16. The device of claim 9, wherein the actuator comprises a syringe.

17. The device of claim 16, additionally comprising a check valve within the bolus flow path, between the syringe and the bolus reservoir.

18. The device of claim 1, wherein said bolus reservoir comprises a spring-biased piston.

* * * * *